(12) United States Patent
Avakian

(10) Patent No.: US 10,730,017 B2
(45) Date of Patent: Aug. 4, 2020

(54) WATER TREATMENT AND DELIVERY SYSTEM FOR DIALYSIS UNITS

(71) Applicant: Manuel S. Avakian, Rego Park, NY (US)

(72) Inventor: Manuel S. Avakian, Rego Park, NY (US)

( * ) Notice: Subject to any disclaimer, the term of this patent is extended or adjusted under 35 U.S.C. 154(b) by 41 days.

(21) Appl. No.: 15/956,407

(22) Filed: Apr. 18, 2018

(65) Prior Publication Data

US 2018/0236404 A1  Aug. 23, 2018

Related U.S. Application Data

(63) Continuation-in-part of application No. 15/267,499, filed on Sep. 16, 2016.

(Continued)

(51) Int. Cl.
*B01D 61/16* (2006.01)
*C02F 1/28* (2006.01)
(Continued)

(52) U.S. Cl.
CPC ........... *B01D 61/16* (2013.01); *A61M 1/1672* (2014.02); *B01D 61/08* (2013.01); *B01D 61/145* (2013.01); *B01D 61/18* (2013.01); *B01D 61/58* (2013.01); *C02F 1/283* (2013.01); *C02F 1/441* (2013.01); *C02F 1/444* (2013.01); *C02F 9/00* (2013.01); *A61M 2206/11* (2013.01);
(Continued)

(58) Field of Classification Search
CPC ...... B01D 61/16; B01D 61/145; B01D 61/58; B01D 61/18; B01D 61/08; B01D 61/025; B01D 2311/2626; B01D 2311/2649; B01D 2311/268; B01D 2311/06; B01D 2311/04; B01D 2311/263; B01D 2313/10; C02F 1/283; C02F 1/444; C02F 1/441; C02F 1/70; C02F 9/00; C02F 2101/38; C02F 2101/36; C02F 2101/12; C02F 2301/022; C02F 2103/026; A61M 1/1672; A61M 2206/11

See application file for complete search history.

(56) References Cited

U.S. PATENT DOCUMENTS 3,560,377 A * 2/1971 Loeffler ............... B01D 63/082
                                                    210/650
4,495,067 A   1/1985 Klein et al.
(Continued)

FOREIGN PATENT DOCUMENTS

GB     2160855 A  *  1/1986  ............. C02F 1/481

*Primary Examiner* — Liam Royce
(74) *Attorney, Agent, or Firm* — Feldman Law Group, P.C.; Stephen E. Feldman

(57) ABSTRACT

The disclosed technology relates to a water filtration and delivery system for a dialysis unit. The water nitration and delivery system including: a laminarizer, the laminizer producing a laminarizer flow; an ultrafiltration unit, the ultrafiltration unit being placed downstream and connected to the laminarizer, the ultrafiltration unit receiving the laminar flow from the laminarizer; and at least one carbon filter, the at least one carbon filter being placed downstream from the ultrafiltration unit, the at least one carbon filter receiving the laminar flow, wherein the laminar flow causes less stress on internal components of the ultrafiltration unit and the at least one carbon filter.

4 Claims, 4 Drawing Sheets

Related U.S. Application Data

(60) Provisional application No. 62/219,874, filed on Sep. 17, 2015.

(51) Int. Cl.
| | |
|---|---|
| *B01D 61/14* | (2006.01) |
| *C02F 1/44* | (2006.01) |
| *A61M 1/16* | (2006.01) |
| *C02F 9/00* | (2006.01) |
| *B01D 61/58* | (2006.01) |
| *B01D 61/08* | (2006.01) |
| *B01D 61/18* | (2006.01) |
| *C02F 1/70* | (2006.01) |
| *B01D 61/02* | (2006.01) |
| *C02F 103/02* | (2006.01) |
| *C02F 101/38* | (2006.01) |
| *C02F 101/36* | (2006.01) |
| *C02F 101/12* | (2006.01) |

(52) U.S. Cl.
CPC ........ *B01D 61/025* (2013.01); *B01D 2311/04* (2013.01); *B01D 2311/06* (2013.01); *B01D 2311/263* (2013.01); *B01D 2311/268* (2013.01); *B01D 2311/2626* (2013.01); *B01D 2311/2649* (2013.01); *B01D 2313/10* (2013.01); *C02F 1/70* (2013.01); *C02F 2101/12* (2013.01); *C02F 2101/36* (2013.01); *C02F 2101/38* (2013.01); *C02F 2103/026* (2013.01); *C02F 2301/022* (2013.01)

(56) References Cited

U.S. PATENT DOCUMENTS

| | | | |
|---|---|---|---|
| 2013/0098816 A1 | 4/2013 | Elfstrom | |
| 2013/0126430 A1* | 5/2013 | Kenley | B01D 61/00 210/638 |
| 2013/0313196 A1* | 11/2013 | Hufen | C02F 1/441 210/652 |
| 2015/0218020 A1* | 8/2015 | Miller | C02F 1/5236 210/724 |

* cited by examiner

WATER TREATMENT AND DELIVERY SYSTEM FOR DIALYSIS UNITS

CROSS REFERENCE TO RELATED APPLICATION

This application is a continuation in part of U.S. patent application Ser. No. 15/267,499, filed Sep. 16, 2016, currently pending, and claims priority to U.S. Provisional Pat. App. Ser. No. 62/219,874 filed on Sep. 17, 2015, both of which are incorporated by reference in their entireties.

FIELD OF THE INVENTION

The subject matter described herein relates to a water treatment and delivery system for dialysis units.

BACKGROUND

Water plays an important, life-sustaining role for dialysis patients. When hemodialysis started to blossom over 25 years ago, many dialysis centers used water right from the tap. It is now known that certain contaminants in water supplies can cause severe complications in dialysis patients. In fact, no municipal water can be considered safe for use in hemodialysis applications in the absence of a treatment system, since some of the most toxic contaminants arise from municipal water treatment practices.

Hemodialysis patients are particularly vulnerable to contaminants in the water used to prepare concentrate and dialysis fluid, or in water used for reprocessing dialyzers. This vulnerability stems from the fact that water is the major constituent of dialysis fluid. Compared with individuals who are not on hemodialysis, hemodialysis patients are exposed to extremely large volumes of water. The estimated water intake of a healthy individual is 2 L per day or 14 L per week. By comparison, during a single dialysis treatment lasting four hours, performed at a dialysis fluid flow rate of 800 mL/min, a hemodialysis patient is exposed to 192 L of water, or to 576 L per week, if treated three times weekly.

Furthermore, hemodialysis patients have inadequate barriers to such contaminants. In healthy individuals who are not on dialysis, the gastrointestinal tract separates blood from contaminants in the water. By comparison, the barrier between blood and water in hemodialysis patients is the membrane within the hemodialyzer through which transfer of contaminants is limited only by the molecular or particulate size of the contaminant. As such, the water used for dialysis patients must be of special quality.

Water purification systems are currently used to purify water to a level determined to be safe for dialysis patients. The critical piece of equipment in these water purification systems is the reverse osmosis (RO) machine, which has proven itself to be the safest, most reliable, and most economical method of purifying water for dialysis.

The Association for the Advancement of Medical instrumentation (AAMI) has set forth water standards as guidelines for dialysis centers to follow. These standards list maximum levels for ions found in water as well as for heavy metals and bacteria. Maximum Allowable Levels (mg/L) as set by the AAMI are as follows: Aluminum 0.01, Arsenic 0.005, Barium 0.1, Cadmium 0.001, Total Hardness 21.0, Calcium 2.0, Calcium as CaC03 5.0, Magnesium 4.0, Magnesium as CaC03 16.0, Chlorine (free) 0.5, Chloramine (combined) 0.1, Chromium 0.014, Copper 0.1, Fluoride 0.2, Lead 0.005, Mercury 0.0002, Nitrate (N) 2.0, Potassium 8.0, Selenium 0.09, Silver 0.005, Sodium 70.0, Sulfate 100.0 and Zinc 0.1.

The current trend is to strive for higher purity for dialysis water while keeping operating cost at a minimum. So, the question remains what is the most reliable and economical way to produce water, which meets or exceeds the AAMI standards?

SUMMARY

The disclosed technology relates to a water treatment system for preserving downstream components, controlling speed and turbulence of the water flow with laminar flow and providing superior water quality.

In one implementation, the disclosed technology relates to a water filtration and delivery system for a dialysis unit. The water filtration and delivery system can include: a laminarizer, an ultrafiltration unit, the ultrafiltration unit being placed downstream and connected to the laminarizer, the ultrafiltration unit receiving a laminar flow from the laminarizer; at least one carbon filter, the at least one carbon filter being placed downstream from the ultrafiltration unit, and at least one horizontal pipe, the at least one horizontal pipe being placed between one of the laminarizer, the ultrafiltration unit and the at least one carbon filter, the at least one horizontal pipe having a downward slope of about 4% thereby enhancing and maintaining the laminar flow.

In some implementations, the laminarizer can include a series of coils in a geometry that initializes the laminar flow as the laminar flow enters the ultrafiltration system.

In some implementations, the at least one horizontal pipe can include a hydraulic bump introduced within the at least one horizontal pipe to further insure the laminar flow is fast and even and prevent hydraulic blockage, in some implementations, the at least one horizontal pipe can include a fish scale pattern within the at least one horizontal pipe to maintain the laminar flow. In some implementations, the at least one horizontal pipe can include be approximately 0.75" in diameter.

The advantage of the disclosed technology is that the water treatment system extends the usable life of carbon filters and RO membranes while providing laminar flow to a dialysis unit.

DETAILED DESCRIPTION

Figure 1:
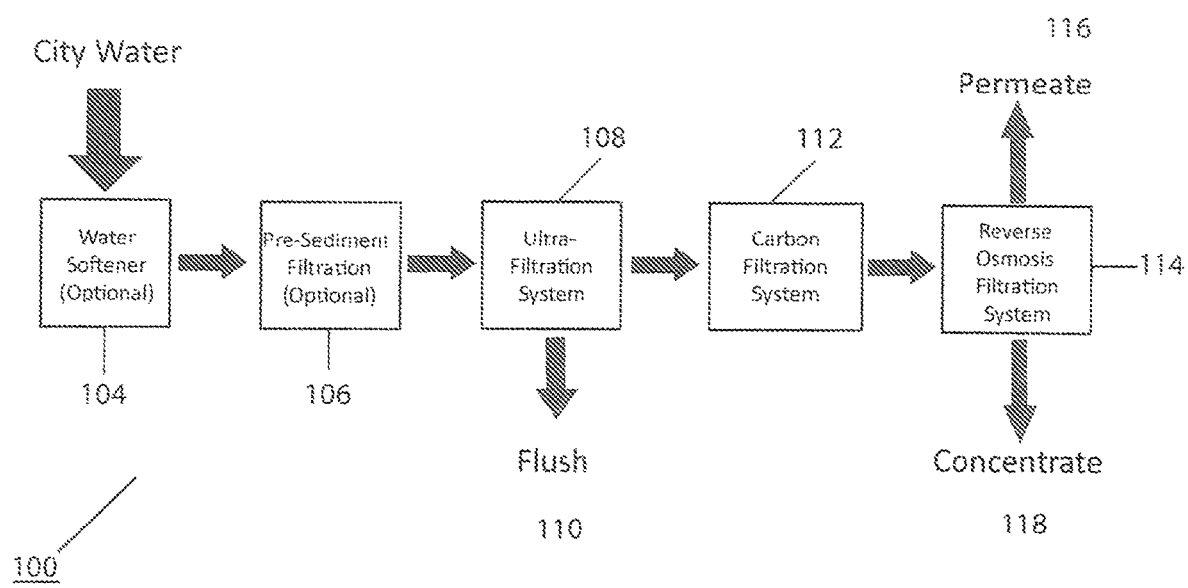
FIG. 1 is a flow chart showing an implementation of the disclosed technology.

The disclosed technology relates to a water treatment system for purifying a water source for dialysis treatments while preserving the life span of downstream filtration system components.

Conventional water purification systems purify water to acceptable levels as set by AAMI but higher purity water for dialysis treatments is constantly being sought. Also, the cost associated with maintaining these conventional water purification systems is high. The cost can be attributed to the replacement and maintenance of the carbon filters and RO membranes. For example, a typical carbon block system must be changed after three months, or in some cases after 7-10 treatments. The RO membranes are replaced after decreased flow product and AAMI chemical analysis indicating unacceptable levels of tested chemicals. The disclosed technology has developed a system that preserves the life span of the carbon filters and the RO membrane by removing suspended solids down to 0.02 μm (micron) in size before the water is fed into the carbon filters and the RO membranes and by the use of laminar water flow. Turbulent flow removes less solids and is rougher on the carbon filters.

The water treatment system 100 can include an ultrafiltration system 108, a carbon filtration system 112 and a reverse osmosis filtration system 114. In some implementations, a pre-sediment system 106 and a water softener system 104 can also be utilized depending on the quality of the water source.

The ultrafiltration system 108 can include an ultrafiltration membrane that provides a physical barrier for the suspended solids and removes particulate from the water source down to approximately 0.02 μm (micron).

These ultrafiltration systems, however, do not remove ions or other elemental forms such as hardness and heavy metals, or small organic molecules such as pesticides.

The advantage of the ultrafiltration system is that the pre-treated water does not contain suspended solids larger than 0.02 μm which in turn puts less stress on the carbon filtration system 112 and the reverse osmosis filtration system 114. Therefore, these carbon filters and RO membranes will have their life significantly increased. For example, the carbon filer system 112 can provide filtration for 100 treatments—a ten-told increase from conventional systems—while the RO membranes are replaced after an AAMI chemical analysis indicates unacceptable levels of chemicals—also a ten-fold increase from conventional systems.

Additionally, the ultrafiltration system 108 can be a backwashable filter that can be flushed periodically, e.g., before each use, allowing the feed water to flush any particulate that has been retained on the ultrafiltration membrane to drain. In some implementations, the ultrafiltration system can have an automated cleaning function set for cleaning the filter after each use. The ultrafiltration system needs replacement when a decreased post ultrafilter pressure indicates decreased product not resolved by cleaning the ultrafilter. Typically, ultrafilters have been providing superior filtration, for over 3 years without a significant decrease in function.

Carbon filters can be used to remove the chlorine and chloramines compounds by chemically reacting with them. The chlorine and chloramines are converted to chloride while the carbon is converted to carbon dioxide. Incoming water passes over the granular activated carbon media inside the tank, then flows up through a tube in the center. During this process, the carbon filter bed does not have to filter any fine sediment, silt, organics and/or dirt as these were removed prior from the water entering the carbon filter.

The reverse osmosis nitration removes both organic molecules and salt ions from the water. In use, an RO membrane sieves organic molecules and repels salt ions while passing pure water through the micropores the RO membrane surface. The driving force behind RO is pressure, which is typically supplied by a centrifugal pump. This pressure is needed to overcome the inherent osmotic pressure of the solution and to supply enough energy to force water through membrane pores which are only about 5 angstroms in diameter.

The basic components of an RO system 114 can be the prefilter, a pump, and sepralators (spiral-wound membrane elements). The sepralators are placed in stainless steel or PVC housings, which are then manifolded together. RO systems 114 operate in a crossflow mode whereby a single stream is fed into the RO and flows across the membrane surface. Two streams exit—the permeate 116 and the concentrate 118. The permeate stream contains the water which passes through the membrane and is purified. The concentrate stream contains the water, salt ions, and organic molecules that do not pass through the membrane; the concentrate is typically plumbed to drain.

The advantage of operating in the crossflow mode is that it minimizes plugging of the very small membrane pores. However, because of crossflow operation, only a percentage of the feed is collected as permeate.

In some implementations, the RO permeate 116 can be fed directly into a loop, which serves the dialyzers. This minimizes stagnant areas where bacteria can establish. In some implementations, the concentrate 118 can be recirculated back to the inlet of the RO. This lowers the feed water dissolved solids level and thus gives an even higher quality permeate.

In use, tap water is fed into an ultrafiltration system 108. The ultrafiltration system 108 removes particulate, down to 0.02 μm (micron) in size. These systems, however, do not remove ions or other elemental forms such as hardness and heavy metals, or small organic molecules such as pesticides. The ultrafiltration system 108 can be flushed periodically in the forward direction by the opening of the solenoid drain valve allowing the flush 110 to exit the ultrafiltration system 108. This allows the feed water to flush the particulate that has been retained on the membrane surface to drain. In some implementations, a 100-200 μm pre-sediment filter, a backwashable sand filter, can be utilized upstream to screen out large particulate, if present. In some implementations, a water softener can also be utilized upstream to remove calcium and magnesium ions.

The treated water from the ultrafiltration system 108 can then be fed to activated carbon tanks 112, employed in series, to remove chloramine, chlorine, and trace organics. It is important to keep the chloramine or chlorine in the system up to this point in order to minimize the chance of bacterial growth.

Next comes the RO machine 114, which typically removes 90% to 95+% of the dissolved salts. RO also removes bacteria and pyrogens as well as 99+% of organic molecules over 200 daltons in molecular weight.

Other important factors to be considered during water treatment and delivery to a dialysis unit is the speed and turbulence of the water passing through the components of the water treatment system. Water flow should be laminar and maintain speeds with little to no turbulence. In other words, the water flow through a passage of a water treatment system should be have a laminar flow at a flow rate that does not to cause turbulence within the pipes as turbulence increases the risk of allowing impurities to enter the pipes as well as degrading the internal components of the carbon filters.

To ensure that the system has laminar flow, start with the Reynold's number, defined as:

$$Re = \frac{\rho v d}{\mu}$$

Where µ is the viscosity of water (0.933 g/ms), d is the diameter of the tube (taken to be 9.525*10^-3 m or 0.375"), ρ is the density of water (100^3 g/m^3), and v is the velocity of the input, or the faucet. Plugging these values in relates the Reynold's number linearly with the input velocity of the faucet. Turbulence is defined as a Reynold's number above 2,000.

$$Re = 10,209v$$

A standard faucet produces a flow between 0.5 gpm and 2.2 gpm and has a diameter of about 0.5" to 0.75". This gives a range of possible input fluid velocities:

$$f = \frac{v_v}{448.8}$$

Where $v_v$ is the volume flow rate in $$\left(\frac{g}{min}\right)$$

and f is the volume flow rate in $$\left(\frac{ft^3}{s}\right).$$

Further as the diameter is given in inches, to get the velocity in $$\frac{ft}{s}:$$

$$v_e = \frac{f}{\pi\left(\frac{d}{24}\right)^2}$$

Where $v_e$ is the flow velocity and d is the diameter of the faucet in inches. Lastly, the flow velocity in the correct units is defined as:

$$v = 0.3048 v_e$$

or $$v = \frac{0.1392 v_v}{d^{\wedge}2}$$

Where $v_v$ is the volume velocity in gpm and d is the inner diameter of the faucet in inches.
1. Faucet Diameter 0.75"
   a. 2.2 gpm produces 0.5444 m/s
   b. 0.5 gpm produces 0.1237 m/s
2. Faucet Diameter 0.5"
   a. 2.2 gpm produces 1.225 m/s
   b. 0.5 gpm produces 0.2784 m/s The Reynold's number for these are as follows:
   1.a 5,558 (turbulent)
   1.b 1,263 (laminar)
   2.a 12,506 (turbulent)
   2.b 2,842 (turbulent)

Therefore, pursuant to a 0.75" faucet diameter, with 0.5 gpm, a laminar flow of 0.1237 m/s is produced.

Alternatively, it may also be necessary to have the water flow at a slight downward angle such as about 4% to provide constant fluid, acceleration that will enable laminar flow through the system, while preventing turbulence resultant from system backflow, Be aware that the rapid laminar flow should not fill the pipes more than half way otherwise there could be an increased chance of the water flow becoming turbulent.

As described above, for effective filtration and delivery for tap water to be used in dialysis unit, the fluid flow in the filters and pipes should be laminar to obtain the best cleaning action and to obtain the fastest flow. In some implementations, to ensure laminar flow, after the water softener and presediment filtration (if used), a laminarizer can be used to convert a turbulent flow into a laminar flow. The laminarizer can use a series of coils with certain geometries to initiate a laminar flow into the downstream filters as well as piping between the filters. These laminar coils convert the flow from turbulent to laminar due to a change in fluid resistance. This is described using Dean's number (K):

$$K = \frac{2r}{R\left(\frac{vr}{\mu}\right)^2}$$

where r is the radius of the cross section, µ is the viscosity of the fluid, v is the velocity of the fluid, and R is the radius of curvature of the coil. Further study extended the understanding of this type of flow, and required the adoption of a new parameter (D) which can be related to K as follows:

$$D = 4K^{1/2}$$

the upper limit of laminar flow is approximately D=5000. To maintain laminar flow entering the second filter, the tube diameter is increased according to:

$$r_2 = \frac{r_1 Re_1}{Re_2}$$

where $r_1$ is the initial tube radius, $Re_1 > 2000$ is the Reynolds number assuming turbulent flow, and $Re_2 < 2000$ for laminar flow.

If the goal is to set $Re_2 = 1,800$, which is within the laminar flow region. Then the radius of the tube into the filter is defined as:

$$r_2 = \frac{\rho r_1^2 v_1}{900\mu}$$

Where $r_1$ is the initial tube length, $v_1$ is the initial fluid velocity, ρ is the density of the fluid, and µ is the viscosity of the fluid.

Design Dimensions:
0.588" is the ID of the inlet nipple. (SST ½" NPT)
27 sq.ft.-membrane area in UF cylinder.
0.9 mm.-multibore membrane ID.
Water pressure is 40 Psi.
Water flow is 72 L/hour×4 hrs.
PESM tubing being used on all lines—0.375" ID.

Given Volume Flow rate =

$$72 \text{ L/hr} \rightarrow 0.317 \text{ gpm} \rightarrow 1.999*10^{-5} \text{ m}^3/\text{s}$$

And volume flow rate = cross sectional area $(CSA)$ * Average fluid velocity $(v)$

Given Tube Diameter = 0.375 in $\rightarrow 9.525*10^{-3}$ m $CSA = 7.1253*10^{-5}$ Average Flow Velocity $(v) = 0.28068$ m/s $rho = 100^3 \frac{\text{g}}{\text{m}^3}$ (standard for water at 20 deg C.)

$\mu = 0.933 \frac{\text{g}}{\text{m}*\text{s}}$ (standard for water at 20 deg C.)

Lastly, $Re = \frac{\rho v d}{\mu}$, so Re=2865, therefore initial flow in pipe is turbulent. From above $$r_2 = \frac{r_1 Re_1}{Re_2}$$

Since the goal is laminar, the laminar to turbulent transition occurs at Re=2000, so take $Re_2$=2000. $r_1$=4.76*10^-3 m. Therefore, goal $r_2$=6.82*10^-3 m or 0.269 in. This gives a tube inner diameter of 0.5381 in.
From above $$K = \frac{2r}{R\left(\frac{vr}{\mu}\right)^2}$$

And $$D = 4K^{\frac{1}{2}}$$

Given the restriction:
Coil diameter no greater than 1 ft, we define R=0.5 ft and: K=43.6449 and D=26.4257.
Both of which are well within the laminar region.

A water treatment system with laminar flow 300 can include a laminarizer 302, an ultrafiltration system 308, a carbon filtration system 312 and piping 314, 416, 318.

The laminarizer 302 can be any component or series of components that causes a water flow to become laminar. In one implementation, the laminarizer 302 can include a series of coils in a geometry that initializes a laminar water flow before the water enters the ultrafiltration system 308, however, other types of laminarizers can be utilized. The advantage of the laminarizer 302 is that when water enters the ultrafiltration system 308 the ore-treated water is flowing in laminar flow and can contain less suspended solids thereby enhancing the filtration of the ultrafiltration unit. The laminarizer 302 and the ultrafiltration system 308 can be connected with piping 314.

The ultrafiltration system 308 can include an ultrafiltration membrane that receives a laminar flow and provides a physical barrier for the suspended solids and removes particulate from the water source down to approximately 0.02 μm (micron).

The combination of the laminarizer 302 and the ultrafiltration system 308 filters solids from the input 304. These solids are usually no larger than 0.02 μm. As mentioned above, this laminar flow also puts less stress on the carbon filtration system 312 and the reverse osmosis filtration system 320 further downstream. Therefore, the carbon filtration system 312 and reverse osmosis filtration system 320 will have their life significantly increased. For example, the carbon filtration system 312 can provide filtration for 100 treatments—a ten-fold increase from conventional systems—while the RO membranes are replaced after an AAMI chemical analysis indicating unacceptable levels of chemicals—also a ten-fold increase from conventional systems.

Additionally, the laminarizer 302 and ultrafiltration system 308 can be a backwashable and flushed periodically (e.g., before each use), allowing the feed water to flush any particulate that has been retained in the laminarizer 302 or on an ultrafiltration membrane. In some implementations, the combination of the laminarizer 302 and the ultrafiltration system 308 can have an automated cleaning function set for cleaning the combination after each use.

The laminarizer 302 also can cause less wear on the ultrafiltration system 308 and the ultrafiltration system only needs replacement when a decreased post ultrafilter pressure indicates decreased product not resolved by cleaning the ultrafilter. Typically, ultrafilters have been providing superior filtration for over 3 years without a significant decrease in function. In other words, the laminarizer 302 will assist in the decrease of wear to the ultrafiltration unit 308.

The carbon filtration system 312 cars be used to remove the chlorine and chloramine compounds by chemically reacting with them. The chlorine and chloramine are converted to chloride, while the carbon is converted to carbon dioxide, incoming water passes over the granular activated carbon media inside the tank then flows up through a tube in the center. During this process, the carbon filter bed does not have to filter any fine sediment, silt, organics and/or dirt, as these were removed prior from the water entering the carbon filter. Additionally, due to the laminar flow, no turbulence enters the carbon filtration system 312 thereby causing less stress on the internal filter components also extending the life of each carbon filter.

The piping 314, 316, 318 between the laminarizer 302, the ultrafiltration system 308 and the carbon filters can be approximately ½" in diameter (although other sizes are contemplated). This piping 314, 316, 318 can have a downward slope such that constant fluid acceleration is maintained with laminar flow through the system, while preventing turbulence resultant from system backflow. That is, the slope causes the water to flow evenly and maintain a fast laminar flow. In most implementations, the flow will fill about half the volume of the piping 314, 316, 318 in order to maintain the laminar flow and the speed of that flow. In some implementations, a fish scale pattern within the piping 314, 316, 318 can be included to maintain the fast laminar flow. In other implementations, a hydraulic bump can be introduced within the piping 314, 316, 318 to further insure fast and even laminar flow and prevent hydraulic blockage.

The reverse osmosis filtration unit 320 removes both organic molecules and salt Ions from the water. In use, an RO membrane sieves organic molecules and repels salt ions while passing pure water through the micropores the RO membrane surface. The driving force behind RO is pressure, which is typically supplied by a centrifugal pump. This pressure is needed to overcome the inherent osmotic pressure of the solution and to supply enough energy to force water through membrane pores, which are only approximately 5 angstroms in diameter.

The basic components of an RO system 320 can be the prefilter, a pump, and sepralators (spiral-wound membrane elements). The sepralators are placed in stainless steel or PVC housings, which are then manifolded together RO systems 320 operate in a crossflow mode, whereby a single stream is fed into the RO and flows across the membrane surface. Two streams exit—the permeate 316 and the concentrate 318. The permeate stream contains the water which passes through the membrane and is purified. The concentrate stream contains the water, salt ions, and organic molecules that do not pass through the membrane; the concentrate is typically plumbed to drain.

The advantage of operating in the crossflow mode is that it minimizes plugging of the very small membrane pores. However, because of crossflow operation, only a percentage of the feed is collected as permeate.

In some implementations, the RO permeate can be fed directly into a loop, which serves the dialysis unit 322. This minimizes stagnant areas where bacteria can establish. In some implementations, the concentrate can be recirculated back, to the inlet of the RO. This lowers the feed water dissolved solids level, thus providing an even higher quality permeate.

In use, tap water is fed into the laminarizer 302. The laminarizer 302 is placed before the ultrafiltration system 308 to begin the laminar water flow in the pipes, with the laminarizer 302 placed before the ultrafiltration unit it will cause the water to begin flowing in a laminar manner to cause even speed in flow rate. The tap water in laminar flow is sent to the ultrafiltration system 308 where the ultrafiltration system 308 removes particulate, down to 0.02 µm (micron) in size. These systems, however, do not remove ions or other elemental forms such as hardness and heavy metals, or small organic molecules such as pesticides. The ultrafiltration system 308 can be flushed periodically in the forward direction by the opening of the solenoid drain valve allowing a flush to exit the ultrafiltration system 308. This allows the feed water to flush the particulate that has been retained on the membrane surface to drain. In some implementations, a 100-200 µm pre-sediment filter, a backwashable sand filter, can be utilized upstream to screen out large particulate, if present. In some implementations, a water softener can also be utilized upstream to remove calcium, and magnesium ions.

The treated water from the ultrafiltration system 308 can then be fed to the carbon filtration system 312, employed in series, to remove chloramine, chlorine, and trace organics. It is important to keep the chloramine or chlorine in the system up to this point in order to minimize the chance of bacterial growth.

Next comes the RO machine 320, which typically removes 90% to 95% to 95+% of the dissolved salts. RO also removes bacteria and pyrogens as well as 99+% of organic molecules over 200 daltons in molecular weight. The treated flow is then sent to the dialysis unit 322

Figure 2:
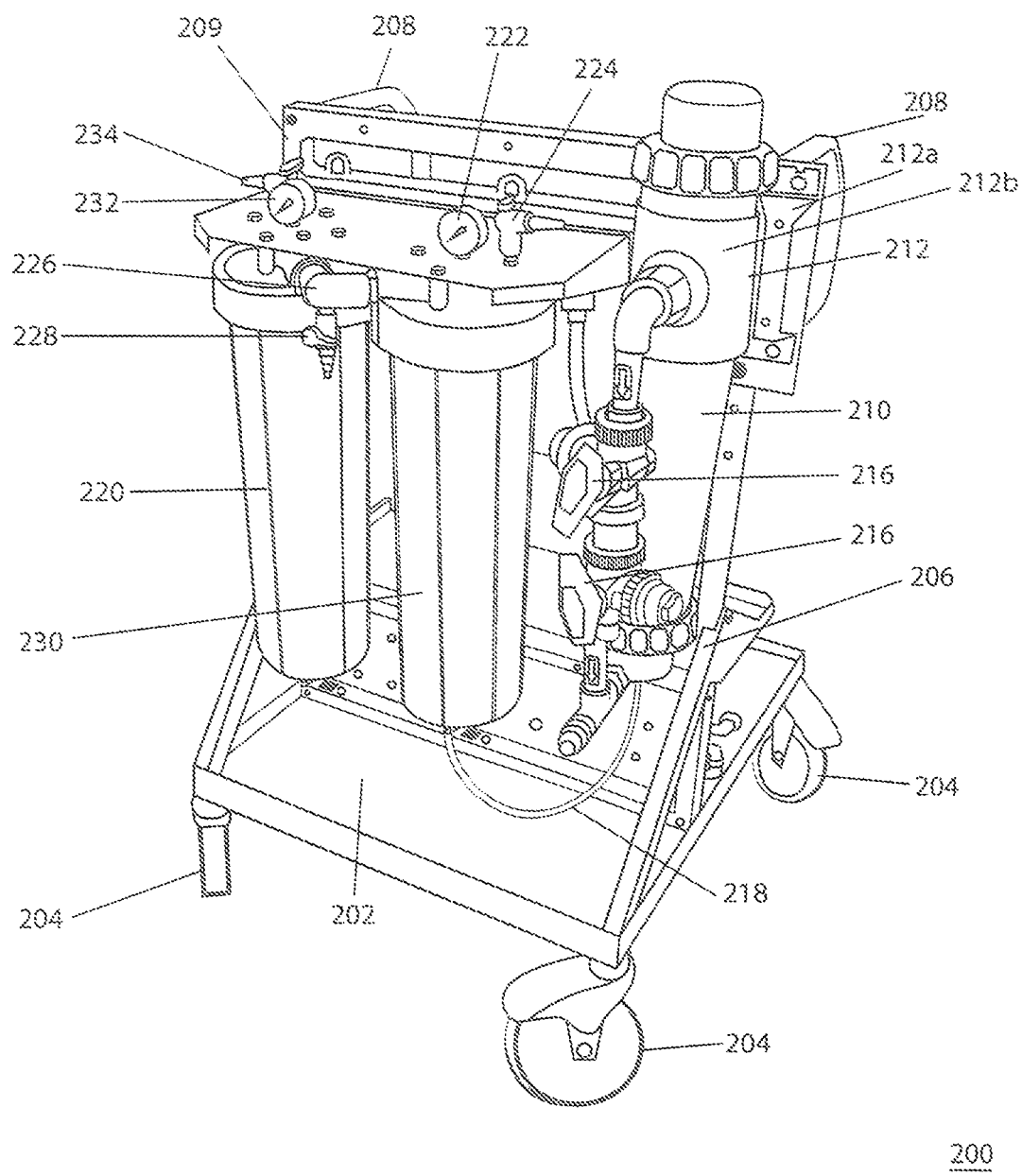
FIG. 2 is a perspective view of an implementation of a water treatment cart of the disclosed technology.
Figure 3:
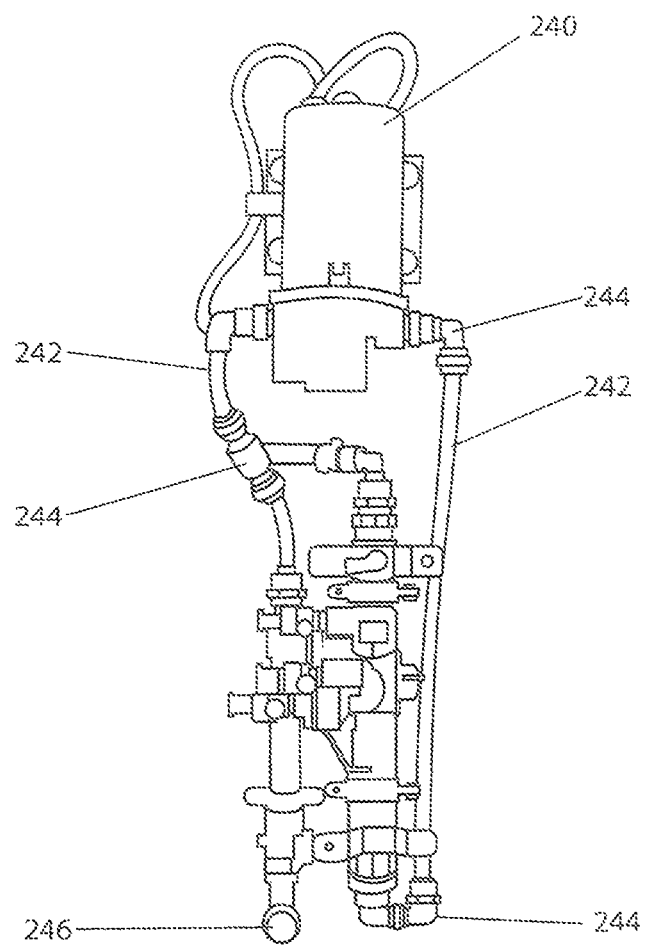
FIG. 3 is a close-up rear view of the water treatment cart shown in FIG. 2.
Figure 4:
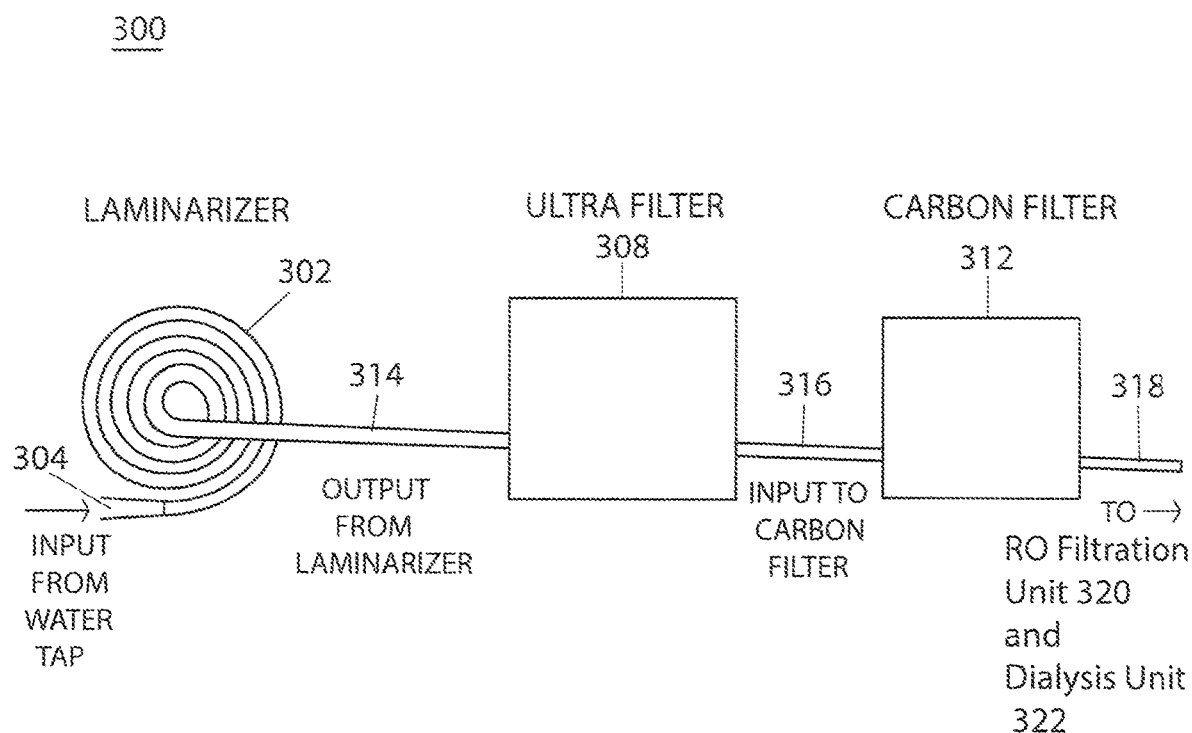
FIG. 4 is a flow chart showing a second implementation of the disclosed technology.

FIGS. 2 and 3 show a water filtration cart 200 employing a portable ultrafilter 210 and two carbon filters 220, 230. This cart 200 can be easily transported and attached to an incoming water source and an RO machine (not shown) in different locations throughout a hospital, home or some other facility and a laminarizer.

The cart 200 also can have a base 202 with caster wheels 204 attached to a bottom thereof. The cart 200 also has supports 206 extending above the base 202 for holding the carbon filters 220, 230 and the ultrafilter 210. The cart 200 can also have handles 208 extending laterally from a top portion of the base supports 206. The laminarizer is placed in the down flow before the ultrafiltration to cause the laminar flow to begin.

The ultrafilter 210 can be attached to the base supports 206 with a mount 212 that surrounds and supports a top portion of the ultrafilter 210 and a rear mount 214 that firmly secures the ultrafilter 210 to the base support 206. The mount 212 includes a flush mount 212a piece rigidly connected to a cylinder mount 212b. The cylinder mount 212b wraps around an outer portion of the ultrafilter 210, while the flush mount 212a mounts to the supports of the cart with nuts and bolts. Hydraulic bumps may be placed in the horizontal pipes to further cause laminar flow and prevent the water flow from suddenly filling a pipe and blocking or interfering with the laminar flow.

The ultrafilter 210 can further include bypass valves 216 used for directing the water flow into a dump, flush or filter positions. The ultrafilter 210 can be communicatively attached to a first carbon filer with tubing 218. The laminarizer combined with the 4% downward flow will cause fast laminar flow.

The first carbon filter 220 can be mounted to a horizontal support 209 extending from the base supports 206. On the top surface of the horizontal supports 209 a pressure meter 222 can be mounted for viewing internal pressures of the first carbon filter 220 along with a sample port 224 for measuring the quality of the water in the first carbon filter 220.

The second carbon filter 230 can also be mounted to the horizontal support 209 having a pressure meter 232 and sample port 234 located thereon. The first and second carbon filters 220, 230 can be communicatively coupled with a bent PVC pipe 226 having a sample port 228 located between the two filters.

The second carbon filer 230 can have a connection for being communicatively coupled to a pump 240 for supplying the water to an RO machine (not shown). The pump 240 can be a high-flow, low-pressure delivery pump located on the base 202 and having tubing 242, fittings 244 and connectors 246 for supplying pressurized treated water to the RO machine.

The disclosed technology preserves the life span of the carbon filters by removing suspended solids down to 0.02 µm (micron) in size before the low particulate water is fed into the carbon filters thereby extending the life of the carbon filters.

The foregoing Detailed Description is to be understood as being in every respect illustrative and exemplary, but not restrictive, and the scope of the disclosed technology disclosed herein is not to be determined from the Detailed Description, but rather from the claims as interpreted according to the full breadth permitted by the patent laws. It is to be understood that the embodiments shown and described herein are only illustrative of the principles of the disclosed technology and that various modifications may be implemented by those skilled in the art without departing from the scope and spirit of the disclosed technology. Those skilled in the art could implement various other feature combinations without departing from the scope and spirit of the disclosed technology. Although the embodiments of the present disclosure have been described with specific examples, it is to be understood that the disclosure is not limited to those specific examples and that various other changes, combinations and modifications will be apparent to one of ordinary skill in the art without departing from the scope and spirit of the disclosed technology which is to be determined with reference to the following claims.

I claim:

1. A water filtration and delivery system for a dialysis unit comprising:
   - a laminarizer, the laminarizer producing a laminar flow;
   - an ultrafiltration unit, the ultrafiltration unit being placed downstream and connected to the laminarizer, the ultrafiltration unit receiving the laminar flow from the laminarizer;
   - at least one carbon filter, the at least one carbon filter being placed downstream from the ultrafiltration unit, the at least one carbon filter receiving the laminar flow, wherein the laminar flow causes less stress on internal components of the ultrafiltration unit and the at least one carbon filter; and
   - at least one horizontal pipe, the at least one horizontal pipe being placed between one of the laminarizer, the ultrafiltration unit and the at least one carbon filter, the at least one horizontal pipe having a downward slope thereby maintaining constant fluid acceleration and preventing turbulence for the laminar flow, wherein the at least one horizontal pipe includes a fish scale pattern within the at least one horizontal nine to maintain the laminar flow.

2. The water filtration and delivery system of claim 1 wherein the laminarizer includes a series of coils in a geometry that initializes the laminar flow before the water enters an ultrafiltration system.

3. The water filtration and delivery system of claim 1 wherein the at least one horizontal pipe includes a hydraulic bump introduced within the at least one horizontal pipe to further insure the laminar flow is fast and even and prevents hydraulic blockage.

4. The water filtration and delivery system of claim 1 wherein the at least one horizontal pipe is approximately ½" in diameter.

* * * * *